(12) United States Patent
van't Hooft

(10) Patent No.: US 8,162,884 B2
(45) Date of Patent: Apr. 24, 2012

(54) APPARATUS FOR INTRODUCING CATHETERS OR NEEDLES INTO A BODY PART

(75) Inventor: Eric van't Hooft, Brasschaat (BE)

(73) Assignee: Isodose Control Intellectual Property B.V., Veenendaal (NL)

( * ) Notice: Subject to any disclaimer, the term of this patent is extended or adjusted under 35 U.S.C. 154(b) by 254 days.

(21) Appl. No.: 11/564,733

(22) Filed: Nov. 29, 2006

(65) Prior Publication Data

US 2008/0262424 A1   Oct. 23, 2008

(30) Foreign Application Priority Data

Nov. 29, 2005   (NL) .................................... 1030553

(51) Int. Cl.
*A61M 5/00* (2006.01)
*A61M 5/32* (2006.01)
(52) U.S. Cl. ........................ 604/116; 604/174
(58) Field of Classification Search .................. 604/116, 604/174–180
See application file for complete search history.

(56) References Cited

U.S. PATENT DOCUMENTS

| 2,177,807 | A | | 10/1939 | Knight | |
|---|---|---|---|---|---|
| 5,938,583 | A | * | 8/1999 | Grimm | 600/7 |
| 6,036,632 | A | * | 3/2000 | Whitmore et al. | 600/7 |
| 6,500,109 | B2 | * | 12/2002 | Tokita et al. | 600/7 |
| 6,579,262 | B1 | * | 6/2003 | Mick et al. | 604/116 |
| 2002/0143229 | A1 | * | 10/2002 | Green et al. | 600/7 |

FOREIGN PATENT DOCUMENTS

EP   1 374 951 A1   1/2004

* cited by examiner

*Primary Examiner* — Nicholas Lucchesi
*Assistant Examiner* — Rebecca E Eisenberg
(74) *Attorney, Agent, or Firm* — Leydig, Voit & Mayer, Ltd.

(57) ABSTRACT

A template, to be provided at some distance from the skin, provided with multiple guide holes for needles or catheters of which one or more can anchor in the prostate. The template is provided with a locking mechanism so that, after placement, the anchored needles keep all needles in their original places. The above-described method of fixedly positioning a treatment template prevents the needles from moving due to swelling of the tissue in the prostate, which causes the irradiation source, which is later provided in the needles, to improperly irradiate the area.

8 Claims, 3 Drawing Sheets

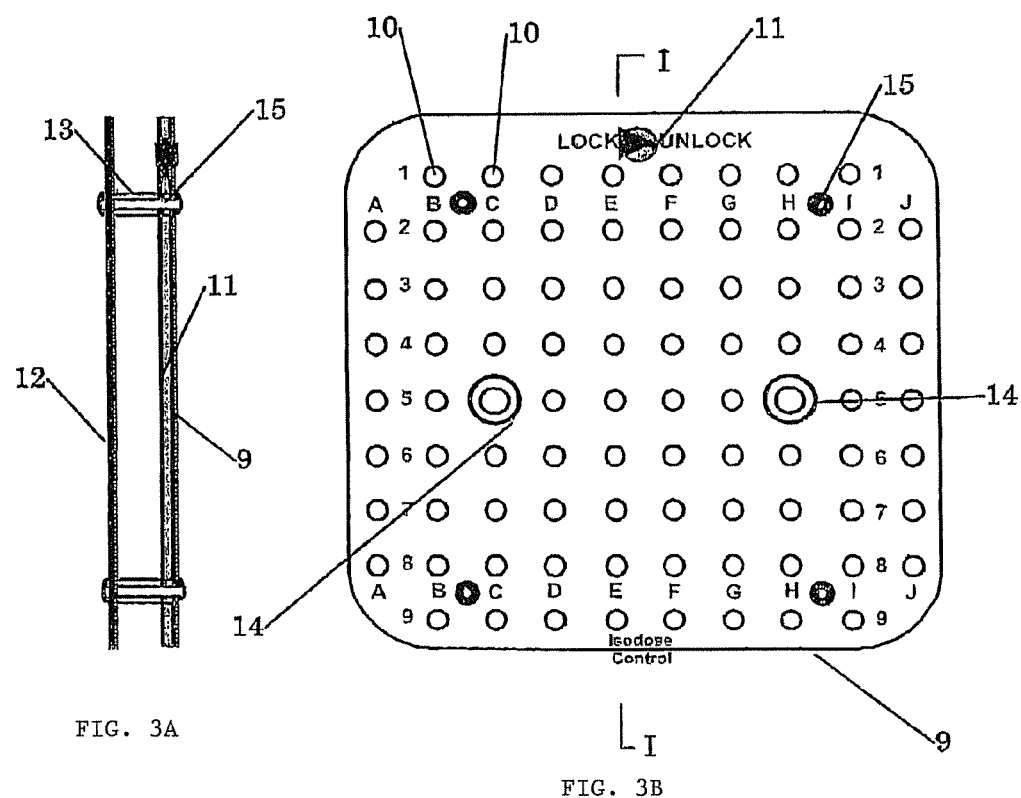
FIG. 3A
FIG. 3B
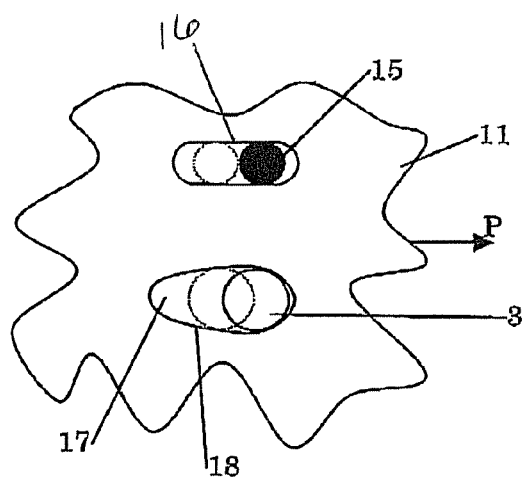
FIG. 4

APPARATUS FOR INTRODUCING CATHETERS OR NEEDLES INTO A BODY PART

FIELD OF THE INVENTION

The invention relates to an apparatus for introducing one or more catheters or needles into a body part.

BACKGROUND

With some therapeutic treatments, in particular irradiating patients for the treatment of tumors, it is necessary to provide a plurality of catheters in the tissue. To this end, the conventional apparatus as, for instance, described in EP1374951 provides a plate part, provided with a number of openings for guiding the catheters and/or needles.

With the treatment of prostate tumors in men, for instance, the conventional use of this apparatus, also referred to as template, is to fix the plate part against the skin and to insert the needles into the prostate with the aid and with guidance of the plate part. After placing the needles, the needles are clamped in the plate part, or a plate part is used which makes it difficult for the needles to move.

Because the plate part is fixed on the skin, with swelling of the tissue—often precisely caused by introducing the needles—the skin will press against the plate part so that the plate part with needles can be pressed away from the prostate up to as much as 20 mm. This can give rise to an undesired situation, which can result in an incorrect irradiation. To correct this, the needles need to be pressed back again regularly or before each repeated irradiation, often with diagnostic guidance. This operation is not only very time-consuming, but also particularly unpleasant and even painful for the patient. In addition, because of the accompanying pain, extra anesthetics often need to be given to the patient.

SUMMARY OF THE INVENTION

It is an object of the invention to be able to offer an alternative to above-described treatment method. To this end, the disclosed apparatus provides a coupling mechanism for a plate part for coupling with at least one anchoring needle for anchoring in the body part for fixation of the plate part with respect to the body part.

As a result, a template can be placed at a large distance from the skin, and the anchoring needles fix the template with respect to the skin. Such anchoring needles, or known construction, typically have an anchoring mechanism for anchoring in the tissue. Typically, such needles potentially include a double wall of which the outer wall has multiple parallel indentations all round so that, upon pulling the inner catheter, the outer wall bends outwards at the location of the indentations so that the catheter locks in the tissue.

Due to fixation of the template by means of the above-mentioned anchoring needles, further, standard catheters can be fixed to the plate part so that the plate part fixes all locked catheters in the same place in a patient's body, such as within the prostate.

BRIEF DESCRIPTION OF THE OF THE DRAWINGS

While the appended claims set forth the features of the present invention with particularity, the invention will be explained in detail with reference to the description of the drawings of which:

FIGS. 3A and 3B depict an embodiment of the apparatus according to the invention;

FIG. 4 depicts a fragment of a locking mechanism for locking the anchoring needle.

DETAILED DESCRIPTION OF THE DRAWINGS

Figure 1:
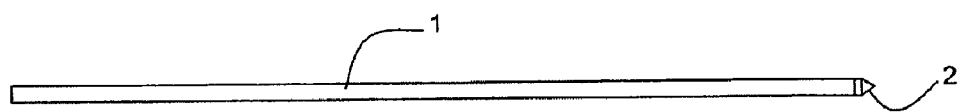
FIG. 1 depicts a conventional catheter.

FIG. 1 shows a conventional catheter 1. The catheter 1 contains a conventional catheter needle 2 that is fed through the catheter 1. Thereafter the needle 2 can be inserted into the tissue through catheter 1. After inserting the needle 2 into the tissue, the needle 2 is removed from the catheter 1 by, for instance, withdrawing it at the backside. Thereafter, the catheter 1 can be connected to a brachytherapy apparatus (not shown), which feeds a radioactive source through the catheter 1 to the position to be irradiated in the tissue. Conventional brachytherapy includes placing a number of catheters in a tissue to be irradiated in predetermined positions, such that the tissue receives a predetermined irradiation dose from radioactive sources that are inserted into the catheters. To this end, normally use is made of a plate part (not shown), which is provided on the skin and fixes the catheters. As discussed hereinabove, use of an unanchored plate has the drawback that, with swelling of the skin and underlying tissues, the position of the catheters in the tissue to be treated can be altered, which adversely affects the effectiveness of the irradiation delivered by the radioactive sources.

Figure 2:
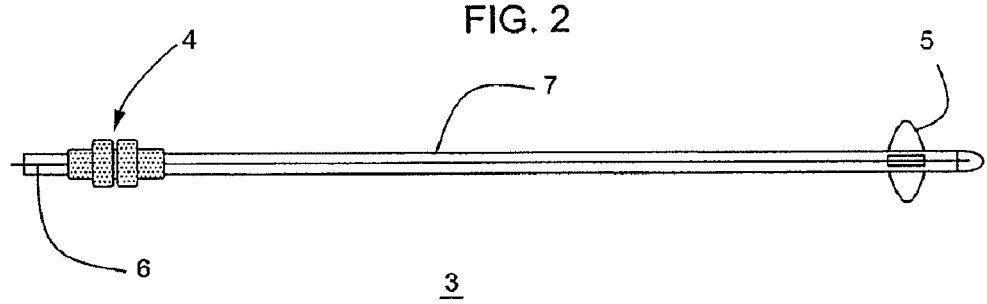
FIG. 2 depicts an anchoring needle.

FIG. 2 depicts a conventional anchoring needle 3 that is used for fixation in a tissue. The anchoring needle 3 typically comprises a fixing part 4 and a laterally movable anchoring element 5 that is anchored in a body part. The element 5 is fixed by rotation or displacement of the fixing part 4. This may be achieved, for instance, by means of a central part 6 that is moved in a tube part 7, and which presses the anchoring element 5, formed by a strip-shaped structure provided in the tube part, laterally outwards upon displacement. FIG. 2 depicts the position of the anchoring element 5 pressed laterally outwards.

FIGS. 3A and 3B depict a template apparatus according to the invention. In particular, FIG. 3A depicts the apparatus in cross section, viewed along the line I-I in FIG. 3B, which shows a top plan view of the template apparatus. According to FIGS. 3A and 3B, the template apparatus comprises a plate part 9 with conventional guide openings 10 as a first coupling mechanism for guiding catheters and/or needles (not shown). A clamping plate 11 controllably locks the needles in the guide openings 10. A further plate part 12 is provided that is kept at a distance from plate part 9 by spacers 13. The plate parts 9 and 12 are manufactured from a relatively light material, such as a plastic, and provide a linear guide for the catheters and/or needles.

The template 8 further comprises two guide openings 14 for guiding two anchoring needles such as the anchoring needle 3 depicted in FIG. 2. The guide openings 14 are centrally placed and form a coupling mechanism different from the first mechanism. By way of example, the clamping plate 11 holds the two anchoring needles (e.g., the anchoring needle 3) in place. Alternatively or in addition, a distinct fixing/holding mechanism may be present to fix the anchoring needles in relation to the plate parts 9 and 12. Thus, by anchoring of the anchoring needles in a body part, the plate part 9 (and the treatment catheters held therein) can be held in fixed position with respect to the body part.

In the example of the drawing provided in FIG. 3B, to this end, two openings 14 are provided in central positions symmetrically with respect to the center. In other embodiments, alternative geometries/arrangements of anchoring needles, such as a triangular arrangement including three anchoring needles, anchor the treatment template apparatus that includes plates 9 and 12 in relation to treated tissue. In one variant, the anchoring needle (e.g., anchoring needle 3) is provided with a hollow structure through which a radioactive source is guided.

As shown, a coupling mechanism/arrangement (for holding the anchoring needles) is formed by the clamping plate 11 in cooperation with the guide openings 14. This coupling mechanism further provides fixing of catheters and/or needles as shown in FIG. 1, by clamping them in a set of openings such as the openings 10 in FIG. 3B. The clamping plate 11 is fixed to the plate part 9 with guides 15.

FIG. 4 schematically shows a fragment of the clamping plate 11. Here, a guide 15 can slidingly move in a slot 16. As a result, the clamping plate 11 moves relative to the plate part 9. A catheter (e.g., catheter 1) or anchoring needle (e.g., needle 3) put through an opening 10 or 14 of the plate part 9 runs through the clamping plate 11, and, for example, through the opening 17. The opening 17 comprises sides 18 which form a running surface, which clampingly abuts a catheter 1 put through an opening of the first plate part 9. In FIG. 4, in continuous lines, a released position is drawn of the needle 3; and, in broken lines, the locked position realized by displacement in the direction of arrow P.

Figure 5:
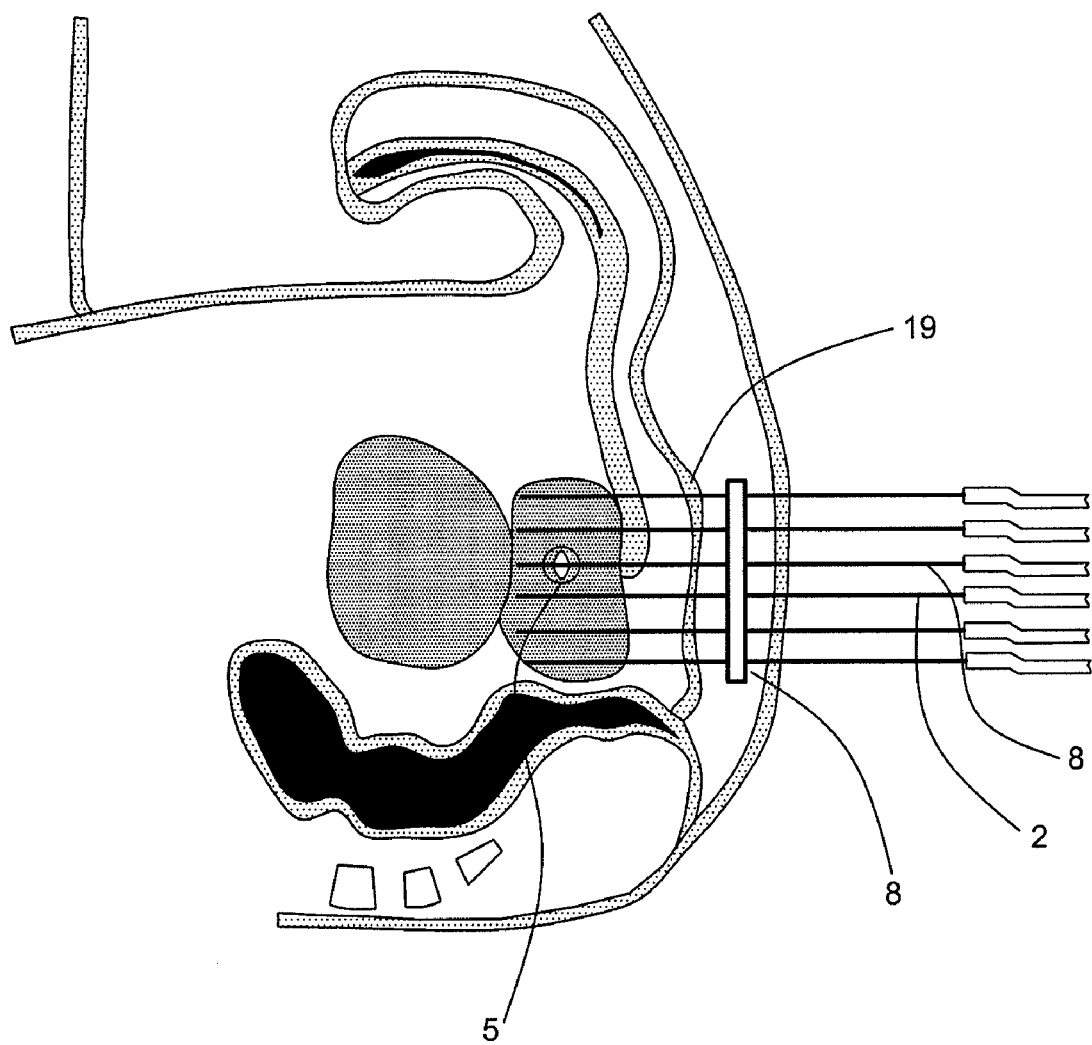
FIG. 5 depicts a side elevational view of the apparatus in use.

FIG. 5 depicts a schematic representation of the template apparatus of FIGS. 3A and 3B in use. In particular, it can be seen how a template 8 is kept at a distance from the skin 19. The template is fixed with respect to the prostate by means of an anchoring needle 3, and in particular the anchoring element 5 of the anchoring needle 3. The anchoring needle 3 is coupled with the template. The template guides catheters 2 and/or needles by means of the template 8 anchored on the prostate.

The invention is not limited to the embodiments shown in the drawing but may also comprise alternatives or variants thereof which fall within the scope of the following claims. Such variants may comprise, for instance, alternative coupling mechanisms, where the anchoring needle is coupled separately from the catheters. In addition, a coupling construction may be provided, for instance, by means of a fastening clip or the like to fix the template 8 on an anchoring needle. The anchoring needle 3 itself may be designed in various manners, as long as an anchoring in the tissue is provided. Such variants are understood to fall within the claims defined in the following.

What is claimed is:

1. An apparatus for introducing one or more catheters or needles or a combination thereof into a body part, comprising:

a first plate part, provided with a first coupling mechanism for coupling and guiding the catheters, needles or combinations thereof, by fixing of the catheters, needles or combinations thereof to the first plate, wherein said first coupling mechanism comprises a plurality of first openings distributed across a substantial majority of the first plate part, for guiding the catheters, needles or combinations thereof, individual ones of the plurality of first openings being a first size;

said apparatus further comprises a second coupling mechanism in the first plate part, different from the first coupling mechanism, the second coupling mechanism constructed for coupling at least one anchoring needle to the first plate part, wherein the second coupling mechanism comprises at least one second opening having a second size differing from the first size of the first openings, the second size being dimensioned in the first plate part to correspond with the at least one anchoring needle and a clamping mechanism for clamping the anchoring needle in said at least one opening, and wherein a first quantity of the total number of first openings in the first plate part are substantially greater than a second quantity of the total number of second openings in the first plate part;

said apparatus further comprises a second plate part and spacers for keeping the second plate part at a distance with respect to the first plate part, wherein the second plate part comprises a plurality of linear guide openings corresponding to the openings provided in the first plate part such that said openings in the first and second plate parts provide a linear guide for the catheters, needles or combinations thereof; and wherein said anchoring needle is constructed for use with said second coupling mechanism so that when said anchoring needle is anchored in the body part said apparatus is fixed relative to the body part by the second coupling mechanism.

2. An apparatus according to claim 1, wherein the first and second coupling mechanisms each comprise a clamping plate which is, parallel to the first plate part, displaceable from a locking position to a releasing position, which clamping plate makes a running surface clampingly abut a catheter or needle put through an opening of the plate part due to displacement.

3. An apparatus according to claim 2 wherein the clamping plate is fixed to the first plate part by guides that permit a linear sliding engagement relationship between the clamping plate and the first plate part.

4. An apparatus according to claim 1 wherein openings of the at least one second opening are placed towards the center of the first plate part.

5. An apparatus according to claim 1 wherein the at least one second opening consists of two openings.

6. An apparatus according to claim 1 wherein the at least one second opening consists of three openings.

7. An apparatus according to claim 1 wherein individual ones of the at least one second opening are sized relatively larger than a size of individual ones of the first openings.

8. An apparatus according to claim 1 wherein the distance between the first plate part and second plate part established by the spacers is greater than a thickness of the second plate part.

\* \* \* \* \*